United States Patent
Reihl et al.

(10) Patent No.: US 7,107,086 B2
(45) Date of Patent: Sep. 12, 2006

(54) DEVICE FOR IN-VIVO MEASUREMENT OF THE CONCENTRATION OF A SUBSTANCE CONTAINED IN A BODY FLUID

(75) Inventors: Bruno Reihl, Wilen Bei Wollerau (CH); Ulrich Haueter, Grosshoechstetten (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 10/236,000

(22) Filed: Sep. 5, 2002

(65) Prior Publication Data
US 2003/0050542 A1    Mar. 13, 2003

Related U.S. Application Data

(63) Continuation of application No. PCT/CH01/00127, filed on Feb. 28, 2001.

(30) Foreign Application Priority Data

Mar. 8, 2000    (DE)    ................................. 100 11 284

(51) Int. Cl.
*A61B 5/00*    (2006.01)
(52) U.S. Cl. ...................... 600/310; 600/316
(58) Field of Classification Search ........ 600/309–310, 600/316, 473, 476, 322, 344
See application file for complete search history.

(56) References Cited

U.S. PATENT DOCUMENTS

| | | | |
|---|---|---|---|
| 4,255,053 A | | 3/1981 | Lubbers et al. |
| 5,101,814 A | * | 4/1992 | Palti ............................ 600/347 |
| 5,342,789 A | * | 8/1994 | Chick et al. ................. 600/322 |
| 5,368,027 A | | 11/1994 | Lubbers et al. |
| 5,560,356 A | * | 10/1996 | Peyman ....................... 600/316 |
| 5,569,186 A | * | 10/1996 | Lord et al. ................... 600/316 |
| 5,833,603 A | * | 11/1998 | Kovacs et al. .............. 600/317 |
| 5,846,188 A | | 12/1998 | Palti |
| 6,011,984 A | | 1/2000 | Van Antwerp et al. |
| 6,256,522 B1 | * | 7/2001 | Schultz ........................ 600/317 |
| 6,285,896 B1 | * | 9/2001 | Tobler et al. ................ 600/338 |

FOREIGN PATENT DOCUMENTS

WO    WO 95/22927    8/1995

OTHER PUBLICATIONS

Webster's II New Riverside University Dictionary, Riverside Publishing Company, 1994, pp. 428 and 988.*

* cited by examiner

*Primary Examiner*—Eric F. Winakur
(74) *Attorney, Agent, or Firm*—Dorsey & Whitney LLP

(57) ABSTRACT

A device for the in-vivo measuring of a constituent of a body fluid, the device including a light emitter which emits light in a wavelength range to which the constituent is sensitive and which is implantable in living tissue, and a light detector which, when the device is in a measuring position, receives the light emitted by the emitter and outputs a signal depending on the amount of light received, from which signal the constituent may be measured, wherein the light detector is situated outside the tissue when the device is in the measuring position.

28 Claims, 2 Drawing Sheets

DEVICE FOR IN-VIVO MEASUREMENT OF THE CONCENTRATION OF A SUBSTANCE CONTAINED IN A BODY FLUID

This is a Continuation Application of International Patent Application PCT/CH01/00127, filed on Feb. 28, 2001, which claims priority to German Patent Application No. DE 100 11 284.6, filed on Mar. 8, 2000, both of which are incorporated by reference herein.

BACKGROUND

The present invention relates to devices and methods for measuring, in-vivo, the concentration of a constituent of a body fluid. In one embodiment, the present invention relates to a device and method for measuring, in-vivo, glucose concentration within the context of diabetotherapy.

Devices used in diabetotherapy for measuring the glucose concentration in the blood or in another human body fluid are based on a chemical reaction between the glucose and a reactant. The diabetic injects himself with a needle under the skin and brings the blood penetrating through the skin at the injection point into contact with the reactant. The reactant is applied to a test strip. The test strip, including the point at which the reaction between the glucose and the reactant has occurred, is inserted into a measuring and evaluation means. A detector which is sensitive to the reaction between the glucose and the reactant records the result of the reaction and outputs a signal dependent on the result of the reaction. The glucose concentration in the blood sample is determined from the signal and optically displayed. More basic measuring devices are based on a color change of the test strip, the tint of the test strip being a measure of the glucose concentration in the blood sample. A disadvantage of the method is that the skin must be broken or injected again for each measurement.

WO 98/01071 describes a measuring device using which the glucose concentration in the blood or in the intercellular fluid can be optically measured. The device comprises a light source and a light detector which operate in the infrared range. The light source and the light detector are implanted in the human tissue. Their arrangement when implanted is such that a decoupling area and a detector area, lying directly opposite each other in the tissue, form a measuring distance between them in which light is absorbed. Light emitted from the decoupling area is absorbed by the detector area, once it has passed along the measuring distance. Infrared light of various wavelengths is used, and evaluated by means of infrared spectroscopy. The degree of absorption of the infrared light is used as a measure of the glucose concentration in the blood. Implanting is complicated and invasive.

SUMMARY

It is therefore an object of the invention to provide a device for measuring a constituent of a body fluid which does not require samples to be taken and which keeps the burden on the user to a minimum.

In one embodiment, the present invention comprises a device for measuring in-vivo the concentration of a constituent of a body fluid, comprising a light emitter which emits light in a wavelength range to which the constituent is sensitive and which is provided to be implanted in living tissue, and a light detector which, in a measuring position of the device, receives the light and outputs a signal depending on the light received, from which signal the concentration of the constituent may be determined, wherein the light detector is situated outside the tissue in the measuring position.

In one embodiment, the present invention comprises a device for the in-vivo measuring of a constituent of a body fluid, the device comprising a light emitter which emits light in a wavelength range to which the constituent is sensitive and which is implantable in living tissue, and a light detector which, when the device is in a measuring position, receives the light emitted by the emitter and outputs a signal depending on the amount of light received, from which signal the constituent may be measured, wherein the light detector is situated outside the tissue when the device is in the measuring position.

The invention is based on a device for measuring in-vivo the concentration of a constituent of a body fluid, comprising a light emitter and a light detector. The light emitter emits light in a wavelength range to which the constituent is sensitive, and is provided to be implanted in living tissue, i.e., it is formed to be histocompatible. The light emitter and the light detector are aligned in the operational or measuring position of the device in such a way that the light detector receives the light from the light emitter. The light detector emits a signal dependent on the light received, from which the concentration of the constituent in the body fluid may be determined. The concentration is determined from the emitted signal by means of a suitable subsequent evaluation means.

In accordance with the invention, the light detector is situated outside the tissue in its measuring position. By permanently positioning the light emitter in the tissue in accordance with the invention, but not implanting the light detector, it is possible to optically measure a physical variable with minimal costs in terms of invasiveness, said physical variable representing a measure of the concentration of the constituent to be determined. It is in this sense that the concentration is measured. The light emitter is advantageously implanted near the surface of the skin, but in such a way that the light from the light emitter penetrates through a layer comprising intercellular body fluid to the external light detector.

The light emitter is arranged under the epidermis. The light emitter is preferably implanted at such a depth that a light emitting area of the light emitter facing the surface of the skin exhibits a distance from the surface of the skin of at most approximately 10 mm, in one embodiment, 7 mm. The minimum distance corresponds to the thickness of the epidermis, i.e. approximately 0.3 mm.

In one embodiment, the constituent whose concentration is to be determined is glucose. However, by appropriately adjusting the wavelength range of the light and appropriately adjusting the light emitter and the light detector, the concentration of a different constituent of the body fluid can also be determined using the device.

The fact that the light relevant for measuring comes from a sensitive wavelength range means that this light interacts with the constituent whose concentration is to be determined, in a way which can be detected by means of the device. This interaction can in particular be that the light is only absorbed by the constituent whose concentration is to be determined, or is only absorbed by the other constituents of the body fluid to a lesser extent, i.e. selective absorption occurs. Instead or in addition, the wavelength range can also be sensitive in the sense that a polarization of the light occurs in this wavelength range which is characteristic of the constituent in question, marked, and therefore detectable.

In some embodiments, when implanted, the light emitter is supplied from outside the tissue with energy for generating the light or is supplied directly with light generated outside the tissue.

In the first variant above, the light emitter which is to be implanted or is implanted in the measuring position is itself a light source and the device further comprises an energy source for supplying this light source with energy. The energy source is not implanted. Energy is supplied by means of an implanted connection line between the energy source and the light emitter, or without a line, preferably inductively.

In the second variant above, the light emitter is a light conductor and the device further comprises a light source for generating the light. In the measuring position of the device, the light source supplies the light outside the tissue into the light conductor. The light source can be connected or is permanently connected to the light conductor. The light conductor is preferably formed by one or more glass fibers. Only the light conductor of the device in accordance with the invention is implanted.

In another exemplary embodiment of the second variant, the light emitter is a reflector and the device further comprises a light source for generating the light, wherein, in the measuring position, said light source emits the light through the skin and the tissue below to the reflector. In the measuring position, the reflector reflects the light received from the light source to the light detector. Using an implanted reflector has the advantage compared to using a light conductor that no connection line from the light emitter to the surface of the skin has to be implanted. Compared to an energy source outside the tissue which wirelessly supplies energy to the light emitter forming the light source, a reflector alone exhibits the advantage that another form of energy in addition to the light is not supplied into the tissue at the measuring point. Furthermore, the path length of the light used for measuring is extended, i.e. interaction with the constituent whose concentration is to be determined occurs over a longer measuring distance. Working back, the implanting depth can be kept to a minimum.

The reflector can be formed as a concentrator, in one embodiment as a parabolic reflector.

In one embodiment, the reflector comprises at least two light-reflective surfaces. In this context, a layer of material of the reflector is also understood as a surface, in as far as reflection occurs in it or is influenced by said layer. One of said at least two surfaces forms a measuring area. The other of the at least two surfaces forms a reference area. In this case, the light detector comprises at least two detector areas, namely, one detector area for receiving the light reflected from the one surface and the other detector area for receiving the light reflected from the other surface. The detector forms a measuring signal from the light reflected from the measuring area and a reference signal from the light reflected from the reference area. The concentration of the constituent is determined by comparing the measuring signal with the reference signal, in particular by forming the difference or the ratio of the measuring signal and the reference signal. In one case, the measuring signal is dependent on the concentration of the constituent and on other influences, in particular the skin characteristics and the characteristics of the surrounding tissue including other constituents of body fluid. In this case, the reference signal is ideally only dependent on the external influences, in particular those mentioned, but not on the concentration of the constituent of interest; it is at least measurably less dependent on the concentration of the constituent of interest than the measuring signal. The influences of the skin in particular are filtered out by means of the reference signal. Alternatively, the measuring area can also be designed such that it only has a marked sensitivity to the constituent of interest, and the reference area does not exhibit this sensitivity or only to a measurably lesser extent.

In one embodiment, the reflector comprises at least two light-reflective surfaces which are different in an optical characteristic relating to the light from the sensitive wavelength range. A first surface of the at least two light-reflective surfaces changes this optical characteristic depending on the concentration of a constituent of the body fluid. The optical characteristic changes depending on the constituent whose concentration is to be measured. In principle, however, it can also change depending on another known constituent whose influence on the light is then filtered out. A second surface of the at least two light-reflective surfaces does not exhibit this dependence on the same optical characteristic of the constituent in question. In one embodiment, the optical characteristic which is changed in this way is the degree of reflection of the first surface and/or a polarization effect. In the latter case, the change in the optical characteristic is the change in the polarization effect of the first surface. The first surface can also be formed such that a number of its optical characteristics are changed depending on the concentration of the constituent in question. Light-reflective surfaces which differ in at least one optical characteristic can be formed by coating or by specifically structuring or by coating and structuring at least one of the surfaces. An optical characteristic can be changed depending on the concentration of a constituent of the body fluid by way of a chemical reaction between the constituent in question and the first surface. However, the optical characteristic is preferably changed merely by the constituent reversibly accumulating on the first surface, i.e., by fixing it without a chemical bond. If the concentration of the constituent in the body fluid wetting the reflector is changed, then the proportional area of the first surface on which the constituent accumulates also changes, and/or the thickness of the layer of accumulated constituent changes. Thus, accumulation is dependent on the concentration of the constituent in question in the body fluid.

In another embodiment, the measuring area and the reference area are arranged on different levels with respect to a common level area. When the reflector is implanted, the common level area is formed by the surface of the skin. When implanted, the reference area is arranged directly under the skin, while the measuring area is arranged some way deeper in the tissue, such that body fluid is available between the lowest layer of skin and the measuring area, in a sufficiently thick layer to be measured.

In some embodiments, the light emitter and the detector are spatially fixed relative to each other in the measuring position, e.g., they are mechanically connected to each other in a selected, relative functional or operational position. A connecting element is preferably connected to the light emitter, said connecting element being implanted together with the light emitter such that it protrudes outwards through the surface of the skin, when the light emitter is implanted. On its portion situated outside the tissue, the connecting element is ready to connect to the detector. The detector can, however, also be connected to the light emitter via the connecting element, before implanting. In one embodiment, a light source or energy source remaining outside the tissue is fixed to the connecting element, in the measuring position. The connecting element can be a simple bolt. Fixing, fastening, mounting, attaching or connecting are intended to comprise conventional fasteners, e.g., bolts, posts, screws, arms, clamps, rivets, flanges, pins and the like. Components may be connected adhesively, by friction fitting, or by welding or deformation, if appropriate.

In one embodiment, the light emitter can be attached to a skin passage device which may be permanently implanted as a body port, for example, for supplying a medicine, or medical or therapeutic fluid long-term. The light emitter is implanted together with the skin passage device and does not need to be implanted separately. Advantageously, the skin passage device can also simultaneously serve as a base platform for the detector and as appropriate also as a base platform for a light source or an energy source serving to supply the light emitter with light or energy from outside the tissue. The light emitter can be an integral component of the skin passage device. An anchoring portion of the skin passage device which serves to anchor the skin passage device in the tissue can in particular form a base platform for the light emitter. One suitable skin passage device is, for example, known from EP 0 867 197 A3, owned by the owner of the present invention. The light emitter can in particular be recessed into the anchoring plate of said skin passage device or can be attached to it. As appropriate, the anchoring plate of said skin passage device should be suitably orientated in the area of a recessed light emitter with respect to the surface of the skin, i.e., orientated parallel to the surface of the skin in particular areas.

The measuring device in accordance with the invention may be used advantageously in a control loop of a pump in an infusion device. U.S. Pat. Nos. 4,585,439 and 6,368,314 disclose devices of the general type which may be used or adapted for use in accordance with the present invention, and their disclosures are incorporated herein by reference. A user preferably always carries the infusion device about his person for continuously or near-continuously administering a medicinal agent. The medicinal agent is administered depending on the measured concentration of a body fluid constituent. One example of an infusion device is an insulin pump. In diabetotherapy, one preferred area of application for the present invention, the glucose concentration is measured or determined using the measuring device, and the pump or a drive of the pump is controlled depending on this. The measuring device serves as an actual value provider. To this end, the output signal of the detector is supplied to an evaluation means, either via a data line or wirelessly, for example by radio. The evaluation means can also be physically connected directly to the detector. It forms an actual value signal from the measuring signal of the detector, for controlling the pump. The pump thus delivers the agent in direct dependence on the variable, which is to be kept within a desired value range. In the case of an insulin pump, this is the glucose concentration. The concentration measured or determined by measurement is thus the control variable for controlling the pump.

DETAILED DESCRIPTION

Figure 1:
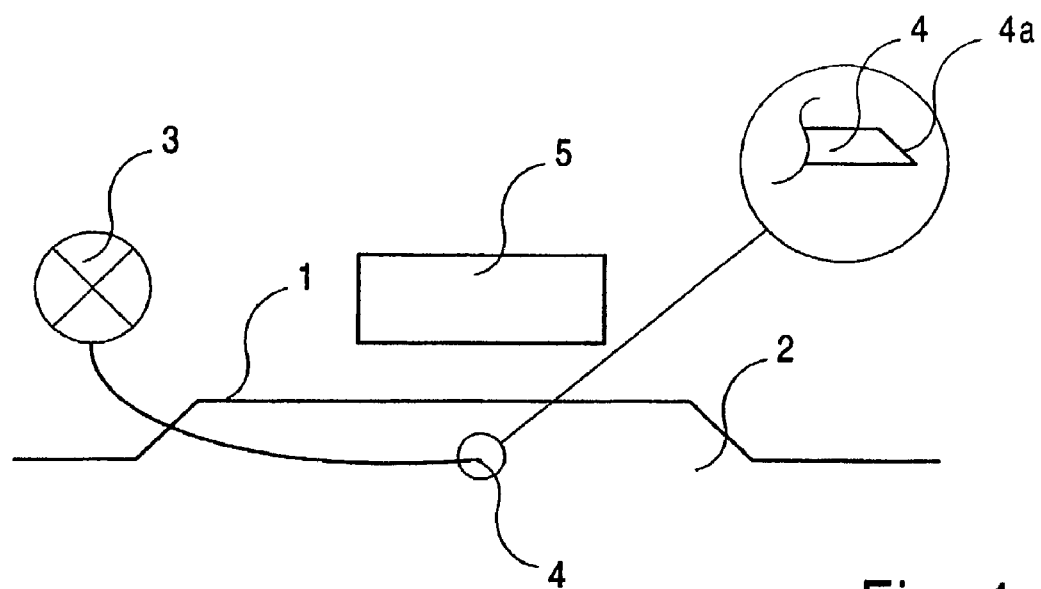
FIG. 1 depicts a measuring device comprising an implanted light wave conductor.

FIG. 1 shows one embodiment of a device for measuring in-vivo the concentration of a constituent of a body fluid. The constituent is glucose and the body fluid is the intercellular fluid in the tissue directly beneath the human skin.

The device comprises a light source 3 which emits white light, a light wave conductor 4 and a light detector 5. The light wave conductor 4, which is, in one embodiment, preferably formed by a glass fiber or a bundle of glass fibers, is implanted in a human tissue 2 under the skin 1 in such a way that a light decoupling point or light emitting area 4a of the light wave conductor 4 is positioned in the tissue comprising the intercellular fluid. The light is emitted at the tip of the light wave conductor 4. The light wave conductor 4 comprises a smooth, oblique profile at its front end, whose exposed profile area, facing the skin 1 when implanted, forms the light emitting area 4a. The light emitting area 4a is shown in the detail in FIG. 1. If the light wave conductor 4 is formed by a bundle of fibers, then its light emitting area is also preferably formed by such a smooth, oblique profile area at the exposed front end of the bundle of fibers. The distance between the light emitting area 4a and the surface of the skin is at least 0.3 mm and preferably not more than 10 mm, particularly preferably not more than 7 mm.

A constant distance, and therefore a constant thickness of the layer of intercellular fluid or a constant length of the measuring distance, is preferably ensured by fixing the emitting area 4a of the light wave conductor 4 to the skin 1 by means of a bolt which simultaneously serves as a spacer. The light wave conductor 4 is guided outwards away from the emitting area 4a, through the tissue 2 and the skin 1, and connected to the light source 3 situated outside the body, for coupling the light. The light detector 5 is arranged directly on the skin 1 above the emitting area 4a, rigidly aligned relative to the emitting area 4a, and facing the emitting area 4a via a detector area. A rigid connection, to fixedly align the detector area of the light detector 5 with respect to the emitting area 4a of the light wave conductor 4, is preferably formed by the cited bolt for attaching the light wave conductor 4. The rigid connection between the light detector 5 and the light wave conductor 4 can be formed to be permanent, or such that it may be detached and repeatedly re-established.

The light source 3 and the light detector 5 are preferably connected to each other in a fixed arrangement, in particular, they may be accommodated in a common casing (not shown).

Figure 2:
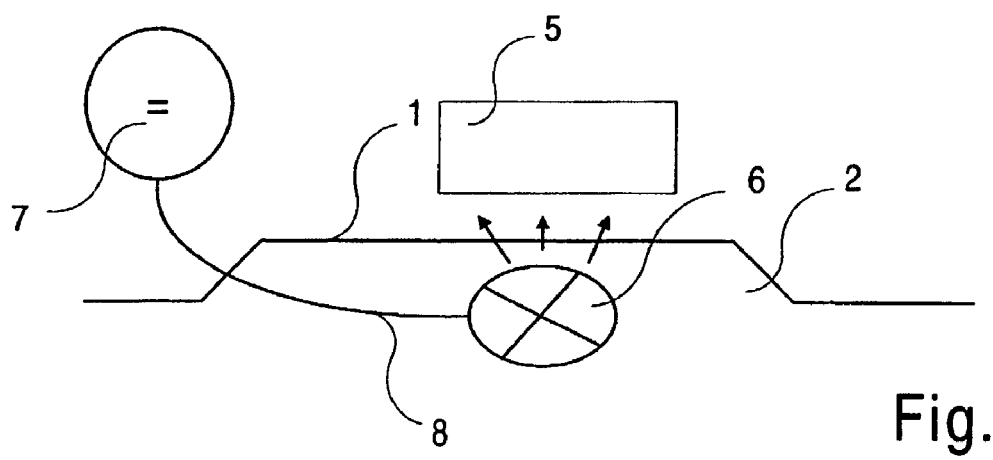
FIG. 2 depicts a measuring device comprising an implanted light source.

FIG. 2 shows another embodiment of the present invention in which a light source 6 is implanted in the tissue 2 underneath the skin 1. The light source 6 can be formed by a light source for white light. Preferably, in one embodiment, it is formed by an infrared laser diode or an array of a number of infrared laser diodes. The implanted light source 6 and the light detector 5 of the embodiment of FIG. 2 are again arranged in a fixed positional relationship to each other and are correspondingly rigidly connected to each other or can be fixed in a rigid connection with respect to each other. The laser diode 6 can again be attached using a bolt, as in the first embodiment. The light source 6 is supplied with energy from an energy source 7, via a line guided outwards through the skin 1. The energy source 7 is formed for example by an electric battery. Instead of a line-bound energy supply, an energy supply without a line, in particular inductively supplying electrical energy, can be provided.

Figure 3:
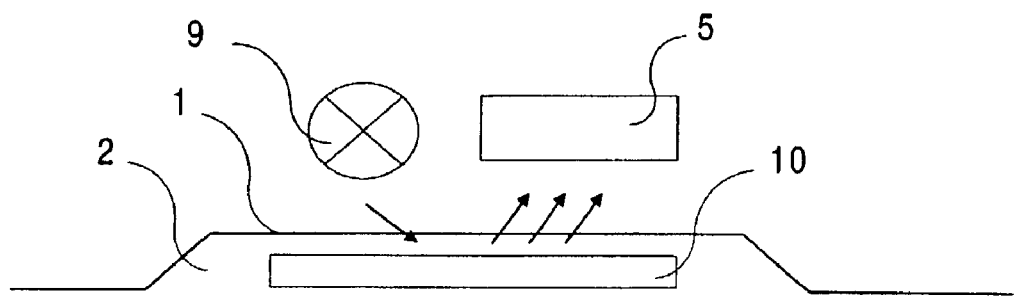
FIG. 3 depicts a measuring device comprising an implanted reflector.
Figure 4:
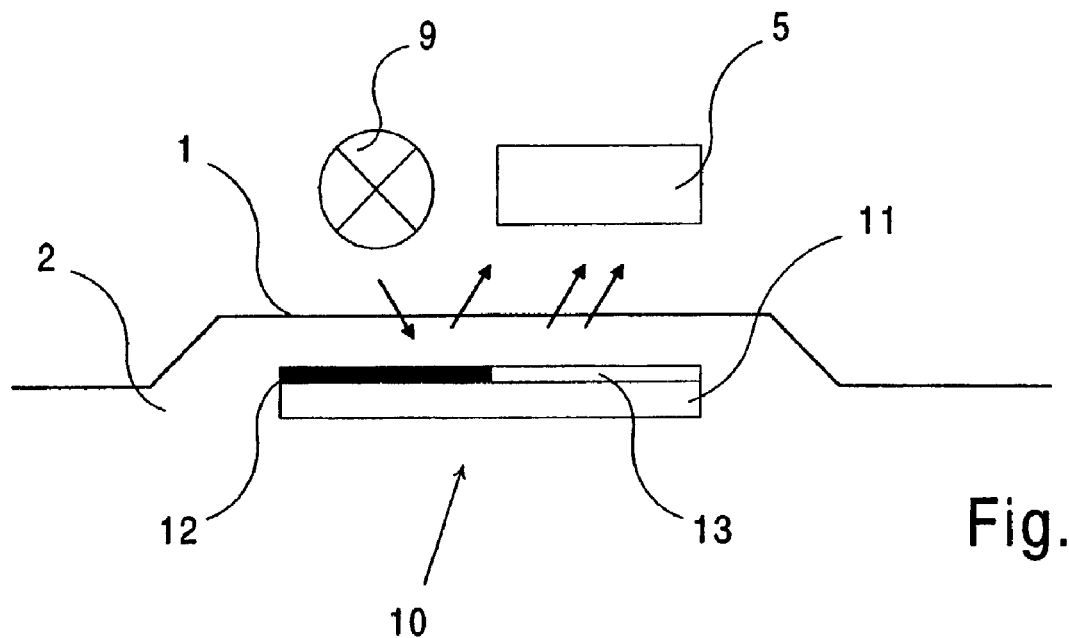
FIG. 4 depicts a measuring device comprising an implanted reflector having two different reflector areas.

In the embodiments of FIGS. 3 and 4, the implanted light emitter is formed by reflectors 10.

The embodiment illustrated in FIG. 3 is a single reflector 10 comprising a single reflector area which faces the skin 1 and is positioned in the tissue 2 parallel to the skin 1. The reflector area extends at least under the epidermis. The reflector 10 serves to reflect the light received from a light source 9 onto the detector 5. The reflector 10 is positioned in the tissue 2 in a fixed positional relationship to the light detector 5 and the light source 9. A rigid mechanical connection preferably exists between these three components, i.e., the light detector 5, the light source 9 and the reflector 10, wherein said connection is preferably permanent, but can, in principle, also be formed such that it can be detached and re-established. The components 5, 9 and 10 can again be fixed in the tissue 2 relative to each other using a bolt.

In this embodiment, the light source 9 emits white light. The light source 9 can equally preferably be formed by one or more monochromatic light sources or by an infinitely variable monochromatic light source. A laser or a laser diode or a laser diode array is preferably used as the monochromatic light source.

A further development of the reflector 10 is shown in FIG. 4. The reflector 10 of the embodiment of FIG. 4 comprises two different reflector area or layers 12, 13. The reflector areas 12, 13 are obtained by coating a reflector base structure 11. The reflector areas 12, 13 comprise different surface structures, in particular different roughness. The surface structures are chosen in such a way that one of the two reflector areas 12, 13, for example, the reflector area 12, changes its degree of reflection depending on the glucose concentration in the intercellular fluid directly bordering the reflector area 12. The change only occurs selectively, depending on the glucose concentration. The other reflector area 13 does not comprise such a surface structure, i.e., its degree of reflection is ideally not dependent or measurably less dependent on the glucose concentration. The two different reflector areas 12 and 13 are arranged side by side on the base structure 11 in such a way relative to the light source 9 and the detector 5 that the path length of the light from the light source 9 to the respective reflector area and from there to the detection area of the detector 5 is on average equally long for the two reflector areas 12, 13. The extent of the change in the degree of reflection is thus determined by measurement and lastly, the glucose concentration in the intercellular fluid above the reflector areas 12, 13 is derived from this. The reflector area 13 serves as a reference area, since all the influences and information area contained in the light reflected by it onto the light detector 5, while the other reflector area 12 forms a measuring area and selectively reacts to the constituent whose concentration is to be determined. By comparing the light signals received from the measuring area 12 with the light signals received from the reference area 13, the extent of the change in the degree of reflection of the measuring area 12 is determined and from this, the concentration of the constituent in question, for example, by forming a ratio or a difference of the two light signals in an evaluation means (e.g., a suitable processor, microprocessor analytical device, etc.) connected to the detector 5. Any suitable evaluation means may be used, including stand alone devices or means that are part of a suitable control system and/or microprocessor(s). As one skilled in the art will recognize, various implementations of program logic are possible, e.g., hardware, software, or a combination of both.

Figure 5:
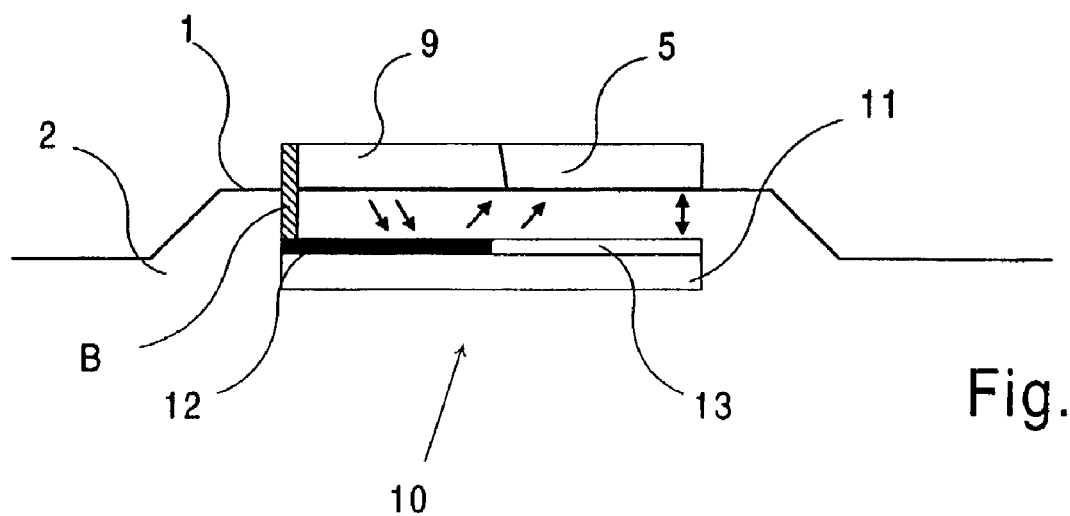
FIG. 5 depicts a measuring device in which a reflector is connected to a detector.

In the arrangement of FIG. 5, a detector 5, a light source 9 and an implanted reflector 10 are connected to each other by a connecting element B. The connecting element B is a connecting bolt which is rigidly connected to the reflector 10 and, when implanted, protrudes up from the reflector 10 and outwards through the surface of the skin. The light source 9 and the detector 5 are fixed to the portion of the connecting element B situated outside the tissue 2. The detector 5, the light source 9 and the reflector 10 can be permanently connected to each other, i.e., not only in the measuring position shown. The detector 5 and the light source 9 could then be connected to the connecting element B by a pivoting connection. After the reflector 10 has been implanted, the detector 5 and the light source 9 fixedly connected to it would be pivoted into the position shown, relative to the reflector 10, and preferably latched in this position. More preferably, however, the detector 5 and the light source 9 are not fixed to the connecting element B, in particular locked into the position shown, until after the reflector 10 has been implanted. The connecting element B can advantageously be formed by a wall or a structural portion of a skin passage device. The components 5, 9 and 10 shown in FIG. 5 correspond, each individually, to the components 5, 9 and 10 of the embodiment of FIG. 4. They can, however, be replaced by the corresponding components of the embodiments of FIGS. 1 to 3.

A light source for white light can be used as the light source in the exemplary embodiments, including the second embodiment comprising the implanted light source. Alternatively, the light source can be a light source for monochromatic light. In this case, a number of monochromatic light sources or an infinitely variable monochromatic light source are preferably used. Laser light is preferably used in this respect, in particular a laser diode or a laser diode array preferably being used as the light source. If the light source is formed by a laser diode array, then the diodes of the array emit infrared light, each at a different wavelength, which once received by the correspondingly adjusted light detector is analyzed by means of infrared spectroscopy, to determine the concentration of the constituent. In principle, however, it is also possible to use LEDs instead of laser diodes. The light source used preferably emits at least in the infrared range or in the near infrared range, i.e., in the wavelength range of 500 to 1200 mm. In the exemplary embodiments, the light source is preferably pulsed, to save energy on the one hand and on the other to keep the heat burden in the tissue to a minimum.

The light detector is preferably formed by an infrared spectrometer in the 500 to 1200 mm range. In principle, however, the light detector 5 can also be formed by a basic infrared detector.

Embodiments of the present invention and methods of their operation and/or use have been presented for the purpose of illustration and description. They are not intended to be exhaustive or to limit the invention to the precise forms disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. The present invention may be used in applications outside diabetotherapy and/or the medical field. For example, it may be used to monitor the presence and/or concentration of biologically important compounds (in addition to glucose, e.g., cholesterol, drugs, hormones, etc.), the condition of tissue being grown in vitro, or in botanical research. It is possible that the emitting menas of the present invention emits other than light, wherein an aspect of the emission is indicative of a characteristic of tissue or material through which it passes. All such modifications and variations are within the scope of the invention as determined by the appended claims when interpreted in accordance with the breadth they are fairly, legally, and equitably entitled.

The invention claimed is:

1. A device for measuring in-vivo the concentration of a constituent of a body fluid, the device comprising:
   a) an energy source adapted to be situated outside living tissue;
   b) a light source powered by the energy source, emitting light in a wavelength range to which said constituent is sensitive, and adapted to be implanted in living tissue; and
   c) a light detector which in a measuring position of said device receives said light and outputs a signal depending on said light received, from which signal the concentration of said constituent may be determined; wherein
   d) said light detector is adapted to be situated outside living tissue in said measuring position, and in said measuring position, said light source and light detector are connected to each other in fixed alignment relative to each other.

2. The device as set forth in claim 1, wherein said light source is operably coupled to a skin passage device, wherein said skin passage device, when implanted, forms a body port for supplying or discharging a body fluid.

3. The device as set forth in claim 1, wherein said light detector is operably coupled to a skin passage device, wherein said skin passage device, when implanted, forms a body port for supplying or discharging a body fluid.

4. The device as set forth in claim 1, wherein said constituent is glucose.

5. The device as set forth in claim 1, wherein the device is adapted for use as a measuring device in a control loop of a pump in an infusion device for administering an agent, wherein said agent is administered in doses depending on the concentration of said constituent.

6. The device of claim 1, wherein the energy source is an electric battery.

7. The device of claim 1, wherein the energy source inductively powers the light source.

8. The device of claim 1, further comprising an electrical line interconnecting the energy source to the light source.

9. The device of claim 1, wherein the light source is an infrared laser diode.

10. The device of claim 1, wherein the light source is an array of a number of infrared laser diodes.

11. A device for measuring in-vivo the concentration of a constituent of a body fluid, the device comprising:
    a light source adapted to emit light;
    a reflector having a reflective area and adapted to be implanted in living tissue, wherein the degree of reflection for a first portion of the reflective area changes depending on the concentration of the constituent and the degree of reflection for a second portion of the reflective area does not change relative to the concentration of the constituent, and wherein the reflective area reflects the light received from the light source; and
    a light detector for placement in a receiving position relative to the reflector and adapted to receive light reflected from the reflector and output a signal depending on the light received, the signal pertaining to the concentration of the constituent.

12. The device as set forth in claim 11, wherein the light detector is adapted to be situated outside living tissue when placed in the receiving position.

13. The device as set forth in claim 11, wherein the light source is adapted to be situated outside living tissue when emitting light towards the reflector.

14. The device as set forth in claim 11, wherein the light source is adapted to be situated outside living tissue when emitting light towards the reflector, the light detector is adapted to be situated outside living tissue when placed in the receiving position, and wherein the light source and/or the detector are not structurally connected to the reflector.

15. The device as set forth in claim 11, wherein the light source is adapted to be situated outside living tissue when emitting light towards the reflector, the light detector is adapted to be situated outside living tissue when placed in the receiving position, and further comprising a connecting element adapted to structurally connect the light source and/or the detector to the reflector.

16. The device as set forth in claim 11, wherein said light source is operably coupled to a skin passage device, wherein said skin passage device, when implanted, forms a body port for supplying or discharging a body fluid.

17. The device as set forth in claim 11, wherein said light detector is operably coupled to a skin passage device, wherein said skin passage device, when implanted, forms a body port for supplying or discharging a body fluid.

18. The device as set forth in claim 11, wherein said reflector is operably coupled to a skin passage device, wherein said skin passage device, when implanted, forms a body port for supplying or discharging a body fluid.

19. The device as set forth in claim 11, wherein the device is adapted for use as a measuring device in a control loop of a pump in an infusion device for administering an agent, wherein said agent is administered in doses depending on the concentration of said constituent.

20. A device for measuring in-vivo the concentration of a constituent of a body fluid, the device comprising:
    a light source adapted to emit light;
    a reflector having a reflective area and adapted to be implanted in living tissue, wherein the polarization for a first portion of the reflective area changes depending on the concentration of the constituent and the polarization for a second portion of the reflective area does not change relative to the concentration of the constituent, and wherein the reflective area reflects the light received from the light source; and
    a light detector for placement in a receiving position relative to the reflector and adapted to receive light reflected from the reflector and output a signal depending on the light received, the signal pertaining to the concentration of the constituent.

21. The device as set forth in claim 20, wherein the light detector is adapted to be situated outside living tissue when placed in the receiving position.

22. The device as set forth in claim 20, wherein the light source is adapted to be situated outside living tissue when emitting light towards the reflector.

23. The device as set forth in claim 20, wherein the light source is adapted to be situated outside living tissue when emitting light towards the reflector, the light detector is adapted to be situated outside living tissue when placed in the receiving position, and wherein the light source and/or the detector are not structurally connected to the reflector.

24. The device as set forth in claim 20, wherein the light source is adapted to be situated outside living tissue when emitting light towards the reflector, the light detector is adapted to be situated outside living tissue when placed in the receiving position, and further comprising a connecting element adapted to structurally connect the light source and/or the detector to the reflector.

25. The device as set forth in claim 20, wherein said light source is operably coupled to a skin passage device, wherein said skin passage device, when implanted, forms a body port for supplying or discharging a body fluid.

26. The device as set forth in claim 20, wherein said light detector is operably coupled to a skin passage device, wherein said skin passage device, when implanted, forms a body port for supplying or discharging a body fluid.

27. The device as set forth in claim 20, wherein said reflector is operably coupled to a skin passage device, wherein said skin passage device, when implanted, forms a body port for supplying or discharging a body fluid.

28. The device as set forth in claim 20, wherein the device is adapted for use as a measuring device in a control loop of a pump in an infusion device for administering an agent, wherein said agent is administered in doses depending on the concentration of said constituent.

* * * * *